United States Patent [19]
Lee

[11] Patent Number: 5,344,403
[45] Date of Patent: Sep. 6, 1994

[54] SIMPLE RETRACTABLE SAFETY SYRINGE

[76] Inventor: Rahnfong Lee, No. 3, Wen Kang St., Lin 29, Chang Nan Tsun, Yuan Chang Hsiang, Yun Lin Hsien, Taiwan

[21] Appl. No.: 73,484

[22] Filed: Jun. 9, 1993

[51] Int. Cl.$^5$ ............................................. A61M 5/00
[52] U.S. Cl. ......................................... 604/110; 604/195
[58] Field of Search ............................... 604/110, 195

[56] References Cited

U.S. PATENT DOCUMENTS

| | | |
|---|---|---|
| 4,643,200 | 2/1987 | Jennings, Jr. .................... 128/763 |
| 4,675,005 | 6/1987 | DeLuccia ........................... 604/110 |
| 4,692,156 | 9/1987 | Haller ................................ 604/195 |
| 4,747,830 | 5/1988 | Gloyer et al. ..................... 604/110 |
| 4,770,655 | 9/1988 | Haber et al. ...................... 604/110 |
| 4,790,822 | 12/1988 | Haining ............................ 604/110 |
| 4,804,370 | 2/1989 | Haber et al. ...................... 604/195 |
| 4,820,275 | 4/1989 | Haber et al. ...................... 604/198 |
| 4,826,484 | 5/1989 | Haber et al. ...................... 604/110 |
| 4,838,869 | 6/1989 | Allard .............................. 604/195 |
| 4,887,999 | 12/1989 | Alles ................................ 604/110 |
| 4,888,339 | 1/1991 | Vadher ............................. 604/197 |
| 4,908,022 | 3/1990 | Haber .............................. 604/195 |
| 4,909,794 | 3/1990 | Haber et al. ...................... 604/195 |
| 4,935,014 | 6/1990 | Haber .............................. 604/195 |
| 4,935,015 | 6/1990 | Hall .................................. 604/195 |
| 4,944,723 | 7/1990 | Haber et al. ...................... 604/110 |
| 4,946,446 | 8/1990 | Vadher ............................. 604/198 |
| 4,950,241 | 8/1990 | Ranford ........................... 604/110 |
| 4,950,251 | 8/1990 | Haining ............................ 604/195 |
| 4,955,870 | 9/1990 | Ridderheim et al. ............. 604/195 |
| 4,966,593 | 10/1990 | Lennox ............................ 604/198 |
| 4,973,316 | 11/1990 | Dysarz ............................. 604/195 |
| 4,978,343 | 12/1990 | Dysarz et al. .................... 604/195 |
| 4,986,813 | 1/1991 | Blake, III ......................... 604/110 |
| 4,994,034 | 2/1991 | Botich et al. .................... 604/110 |
| 4,995,874 | 2/1991 | Strickland ........................ 604/110 |
| 5,000,738 | 3/1991 | Covollo et al. .................. 604/110 |
| 5,030,209 | 7/1991 | Wanderer et al. ............... 604/198 |
| 5,046,508 | 9/1991 | Weissler .......................... 128/763 |
| 5,053,010 | 10/1991 | McGary et al. .................. 604/110 |
| 5,066,281 | 11/1991 | Stevenson-Michener ........ 604/110 |
| 5,067,942 | 11/1991 | Jaffe et al. ....................... 604/110 |
| 5,088,986 | 2/1992 | Nusbaum ........................ 604/195 |
| 5,098,402 | 3/1992 | Davis .............................. 604/110 |
| 5,112,315 | 5/1992 | Gloyer et al. ................... 604/195 |
| 5,112,318 | 5/1992 | Novacek et al. ................. 604/240 |
| 5,114,404 | 5/1992 | Paxton et al. ................... 604/110 |
| 5,122,124 | 6/1992 | Novacek et al. ................. 604/195 |
| 5,149,323 | 9/1992 | Colonna .......................... 604/110 |
| 5,152,750 | 10/1992 | Haining ........................... 604/110 |
| 5,163,907 | 11/1992 | Szuszkiewicz ................... 604/110 |
| 5,188,601 | 2/1993 | King ................................ 604/110 |
| 5,205,823 | 4/1993 | Zdeb ............................... 604/110 |
| 5,215,524 | 6/1993 | Vallelunga et al. .............. 604/110 |
| 5,242,400 | 9/1993 | Blake, III ......................... 604/110 |
| 5,242,402 | 9/1993 | Chen ............................... 604/110 |

*Primary Examiner*—Paul J. Hirsch
*Attorney, Agent, or Firm*—Jacobson, Price, Holman & Stern

[57] ABSTRACT

A retractable safety syringe has a hub at the end of its plunger which engages a needle carrier when the plunger is depressed so that the needle carrier can be withdrawn into the syringe along with the needle. To facilitate breaking off the plunger shaft, thereby trapping the spent needle within the syringe, there is a conically shaped flangible section between the plunger and the shaft which defines a sharp notch allowing the shaft to be broken off at any angle.

6 Claims, 3 Drawing Sheets

SIMPLE RETRACTABLE SAFETY SYRINGE

BACKGROUND OF THE INVENTION

It is well know that needle stick injuries by protruding needle cannula can result in innocent transmission of hepatitis B and AIDS (acquired immune disease syndrome). There have been several known cases of death resulting from accidental needle stick with contaminated needles. With the advent of the up to now incurable AIDS disease, there is an ever growing concern for a safer medical device to substantially reduce the possibility of hospital personnel being injured by the protruding needle during and after use. Also in order to prevent the spread of disease among drug abusers sharing the same syringes, a safer syringe against needle transmitted diseases is required.

There has been a lot of efforts in our hospitals to educate hospital personnel to take every possible caution to prevent needle stick injuries and to take appropriate medical treatments after needle-stick. However, a more fundamental solution to prevent the injuries as strongly recommended by senior medical professionals, is to develop a new syringe with improved structures which eliminate the operation procedures mostly responsible for the currently reported injuries cases. As a result, until the end of 1992, there have been over 50 U.S. patents disclosing various devices to prevent the sharp needle cannula from coming in contact with human skin. These devices generally fall into two catagories.

The first of the two catagories involved sheathing the needle cannula with an extra plastic tube slidable axially along the syringe barrel and which can be locked in the desired position to protect the sharp needle point from sticking whoever is using and disposing of the syringes, during or after use. The second category falls into a device for retracting the needle cannula into the syringe barrel after use in order to eliminate recapping the needle after an injection and to eliminate disposing of the protruding needles in the waste container. Representative examples with a device capable of retracting the needle and S the needle carrier into the barrel are U.S. patents to John E. Hall, U.S. Pat. No. 4,935,015; Walter W. Gloyer, U.S. Pat. No. 5,112,315 and No. 4,747,830; Michael L. Haining, U.S. Pat. Nos. 4,950,251 and 4,790,822 and 5,152,750; Dinesh L. Vadher, U.S. Pat. Nos. 4,988,339; Laurel A. Novacek, U.S. Pat. No. 5,030,209; Joseph W. Blake, U.S. Pat. No. 4,986,813; Edward D. Dysarz, U.S. Pat. Nos. 4,973,316 and 4,978,343; and Lynn E. Davis, U.S. Pat. No. 5,098,492. Other representative examples of being able to retract only the needle, without a needle carrier into the barrel, are U.S. patents to Christine M. Szuszkiewicz, U.S. Pat. No. 5,163,907; Michael J. Nusbaum, U.S. Pat. No. 5,088,986; James Deluccia, U.S. Pat. No. 4,675,005; Terry M. Haber, U.S. Pat. Nos. 4,770,655 and 4,804,370 and 4,813,426 and 4,820,275 and 4,826,484 and 4,935,014 and 4,909,794 and 4,908,022; Edward F. Allard, U.S. Pat. No. 4,838,869; Alan B. Ranford, U.S. Pat. No. 4,950,241; Dinesh L. Vadher, U.S. Pat. No. 4,946,446; Kristen A. Ridderheim, U.S. Pat. No. 4,955,870; James J. Lennox, U.S. Pat. No. 4,966,593; R. Kern McGary, U.S. Pat. No. 5,053,010; Richard A. Jaffe, U.S. Pat. No. 5,067,942; Deborah G. C. Stevenson-Michener, U.S. Pat. No. 5,066,281; Gerald R. Paxton, U.S. Pat. No. 511,404; Jonathan Weisslet, U.S. Pat. No. 5,046,508; Morris. J. Baskas, U.S. Pat. No. 4,955,870; Michael J. Botich, U.S. Pat. No. 4,994,034; Baldwin P. Jennings, U.S. Pat. No. 4,643,200; Irene Haller, U.S. Pat. No. 4,692,156; Laurel A. Novacek, U.S. Pat. Nos. 5,112,318 and 5,122,124.

Nevertheless, those patents having a device capable of retracting only the needle, without the carrier, such as those disclosed in U.S. Pat. Nos. 5,163,907, 5,088,986, 4,675,005 . . . , 5,112,318 and 5,122,124 have several drawbacks, which are either too complicated structure or having too many components to be made at competitive prices against the currently available syringes, or practically impossible to function properly, although seemingly applicable theoretically. For example, in order to inject the medication or fluid into the huamn tissue, the frictional force between the needle and the plastic embedding it must be large enough to ensure that the needle will not retract prematurally when puncturing the skin for injection prior to intended retraction after use. Since the contact area between the needle and the plastic embedding the needle is very small, from the mechanics points of view, the frictional coefficient between the needle and the plastic has to be very large which is very difficult since, in order to reduce the pain of puncture, a thin silicon film is already on the needle to reduce the frictional coefficient, and that is contradictory to the requirement of the design with retractable needle. Moreover, in the manufacturing processes, it is practically impossible to assemble the needle into the tiny hole of the plastic barrel without very precise instruments and extreme care, to prevent damage of the tip of the needle. The industries can hardly manufacture these syringes at competitive prices with mass production. Although others proposed a screw locking device, for example, James Deluccia, U.S. Pat. No. 4,675,005, however, it is practically very inconvenient for a big hand to rotate a tiny plunger several turns in order to retract the needle. In addition, screws on injection molded parts makes them slow in production and expensive.

Those patented designs with needle and carrier retracting into the barrel after use are free from the above mentioned drawbacks and are more likely to be accepted if the structure is simple and the cost is truely competitive. Edward D. Dysarz, U.S. Pat. Nos. 4,978,343 and 4,973,316 disclosed a design with a spring to assist retracting the needle into the barrel, which was a two piece structure connected in one supposedly by untrasonic welding. However, this structure required more intensives labor to assemble and thus higher costs and furthermore, it required extreme care and costly precision instruments to install the needle in place without damaging the needle tip. Walter W. Gloyer, U.S. Pat. Nos. 5,112,315 and 4,747,830 and Dinesh L. Vadher, U.S. Pat. No. 4,988,339 also disclosed syringes with retractable needle carrier. Nevertheless, the structures were still too complicated with redundant structural elements to be manufactured at very competitive prices. Alternative designs were proposed by Joseph W. Blake, U.S. Pat. No. 4,986,813, in which the needle cannula was screwed onto the base of the barrel. The processes of assembly requires that the needle have no protection cap on the needle tip to guard against tip damage. Despite the fact that the structures of the plunger and the barrel were very complicated and expensive to make, the retracted needle engaged on the plunger after retraction may still easily fall off due to vibration and might protrude out of the open end of the barrel and incidentally injure whoever touches it. Another patented design by Laurel A. Novacek, U.S. Pat. No. 5,030,208 disclosed a too complicated structure with redundant elements and hence higher costs. The needle engaged and retracted by the plunger could still fall off accidently with vibration. Lynn E. Davis, U.S. Pat. No. 5,098,402, proposed another syringe design with retractable needle. Regretfully, it involved too many little components making assembly processes tedious and time consuming. From the functional points of view, the requirement to rotate the tiny plunger with force in order to undo and retract the needle into the barrel is very inconvenient in practice. During this rotational processes, the fragile section on the plunger could be broken by shear force due to the resistance arising from the tight engagement between the needle and the barrel to prevent medication or fluid leakage. In this design, the needle after retraction can still fall off the carrier inside the barrel and moves freely and even comes out of the barrel to injure whoever touches it.

A further patent design as disclosed by Richard C. Terrill, U.S. Pat. No. 4,978,340 also has several disadvantages. The needle tip was not well protected with a cap when assembling the needle onto the barrel, and hence extreme caution is required. In addition to the fact that the structure is complicated, requiring expensive tooling, a more serious problem is that after the retraction of the needle into the barrel either the needle can easily fall off the needle carrier and move freely or the needle carrier can easily disengage itself from the plunger since there is no permanent engagement device between them. The needle could easily injure people. The problems associated with the patent by John E. Hall, U.S. Pat. No. 4,935,015 are similar to the above mentioned designs. The needle tip without a cap to protect from damage during assembly of the needle onto the barrel requires extreme caution and expensive precise instruments. Moreover, since the needle is tightly engaged with screws on the distal end of the barrel to prevent leakage of medication or fluid, in the process of retracting the needle into the barrel by twisting the plunger, the fragile section on the plunger could easily be broken and hence could not retract the needle. Even if the needle is successfully retracted into the barrel, the engagement device between the needle and the plunger is too weak to permanently secure the needle from falling off the plunger. Therefor, these is also a potential danger for needle stick injuries even after needle retraction.

Furthermore, since plastic materials are very notch sensitive, the ease to break the plunger depends upon the notch tip at the fragile section on the plunger. John E. Hall's design of the plunger has directional problems around the plunger. This means that if bending force is applied between the flanges along the plunger, several bendings may be required to break the plunger and these repeated bending may disengage the needle from the plunger momentarily. Screws existing inside the distal end of the barrel also results in slow production, expensive parts and shorter tooling life due to more serious tooling wear.

The inventions by Michael L. Haining, U.S. Pat. Nos. 4,790,822, 4,950,251 and 5,152,750 also have several drawbacks which keep these designs away from being a safer device. As a matter of fact, the manufacturer and the end user can hardly tolerate a safer device being more expensive than the currently available syringes Haining's design also required more component parts and hence was more expensive than the commercially available syringes. Yet, his design wasn't really safer since it didn't actually resolve all the problems. In his design, as the plunger is pushed to a stop but before it pushes further to engage with the needle carrier for retracting the needle into the barrel, the syringe is pulled out of the skin of the patient being injected, because this further push really hurts the patient. In the meantime, the dead space between the carrier and the plunger carrying significant amount of expensive residual medication or fluid is hence wasted. This could waste significant amounts of expensive medical resources, considering the number of syringes used every year. Furthermore, the notch on the plunger is a very poor design, from the mechanics points of view. In order to easily break the plunger, the notch tip has better be as sharp as possible and be sharp all around. Haining's design of the plunger made it difficult to break the plunger easily since stress concentration could not be effectively generated on the notch tip in any direction the plunger may be rotated. The result is that you will in some cases have to repeatedly break the plunger several times, which creates problems, in that during the repeated binding processes of the plunger, the needle on the carrier will be forced to heavily touch the inner wall of the barrel several times and that will loosen the needle from the carrier. It happens quite often that the needle will fall off the carrier and injure whoever touches it, because there is no way to guarantee that the needle will stay permanently together with the carrier inside the barrel no matter what happens and consequently this is not a really safe design. It is therefore the intention of the invention to come up with a new design of syringe with retractable needle, which is simple in structure using the same number of component parts as the currently available syringe, and which costs no more than the current syringes. Yet it has all the desired retractable function, without any foreseeable drawbacks as discussed above. This new design should be able to be produced and used without special care or caution and it requires no skillful workers and expensive instruments to assemble. The dead space carrying the residual medication or fluid should be no higher than the current type. Furthermore, the needle should not fall off the carrier to injure people by any chance no matter what happens. It is also the intention of the invention to develop a syringe with retractable needle substantially free from all the above mentioned disadvantages or other foreseeable drawbacks.

SUMMARY OF THE INVENTION

The present invention relates to a hypodermic safety syringe with retractable needle which is designed to have the same number of component parts as the currently available non-retractable syringe and costs no more than the traditional syringes. Yet, it is equipped with all the desired characteristics an ideal retractable syringe should better have without any other foreseeable drawbacks. It requires no precise, expensive instruments to assemble and no special caution when using it.

This syringe comprises a hollow cylindrical barrel having open ends at both ends, with a finger flange at the upper end and a collar at the lower end, namely distal end. A rigid needle carrier made of plastics seated inside the collar of the lower end of the barrel, with a projection extending out of the barrel. Within this projection holds a needle. This needle carrier holding a needle as an integral piece has an annular groove to engage with the annular bore on the inner wall of the distal end of the barrel, and has a close fit with barrel to prevent leakage of medication or fluid and to provide the carrier with necessary resistance against going backwards into the barrel while withdrawing medication or injecting the needle into human tissues. A plunger is slidably mounted inside the barrel, and the space between the carrier and the lower end of the plunger inside the barrel defines the fluid chamber. This plunger terminated with an elliptical hub at the lower end, which is to be engaged with and locked onto the bore inside the carrier. A rubber seal is located around the shaft between the hub and the end of the plunger. At the end of the injection processes, the plunger is pushed to near the lower end of the barrel and a further push engenders the hub of the plunger to click and lock onto the carrier. Then the plunger is pulled backwards towards the upper end of the barrel, with the carrier attached on the hub. As the plunger reaches the limit of the upper end of the barrel by a bore inside a barrel, the plunger is then broken off at the fragile section on the plunger, leaving the carrier and the broken part of the plunger in the barrel and allowing no chance for the needle to leave the barrel and injure whoever touches the disposed syringes. As to a barrel with large volume capacity, say 20 c.c. for example, the needle is located eccentric to the center of the barrel and the open end of the barrel is eccentric as well. Its mechanisms and operational procedures are basically the same as a smaller barrel having coaxial or concentric opening as described above.

The present design of the invention comprising only four elements, as with the current commercially available non-retractable syringes, is price competitive, in addition to all the extra retractable characteristics to guard against needle sticks associated with our new syringe design. Our syringe with retractable needle will not cost more than the current non-retractable type, due to the same number of component parts, and it requires no special attention since the needle cap can be always on the needle during the assembly processes. The plunger is designed to have a fragile section which can be easily broken off at any angle around the shaft. Dead space between the carrier and the hub is minimized to be no greater than the current non-retractable syringe to prevent too much waste of medication or fluid. Yet, since hub is elliptical in shape, there is sufficient space to accommodate the residual air, if present, within the medication or fluid.

Furthermore, the unique design with the needle on the carrier in one integral piece not only reduces material costs but also permanently prevents the needle from falling off the carrier after retraction.

All these features distinguish this design from the other prior disclosed patents.

DETAILED DESCRIPTION OF THE PREFERRED EMBODIMENT

For a detailed description of the preferred embodiment the reader is directed to the accompanying figures in which like components are given like numerals for ease of reference.

Figure 1:
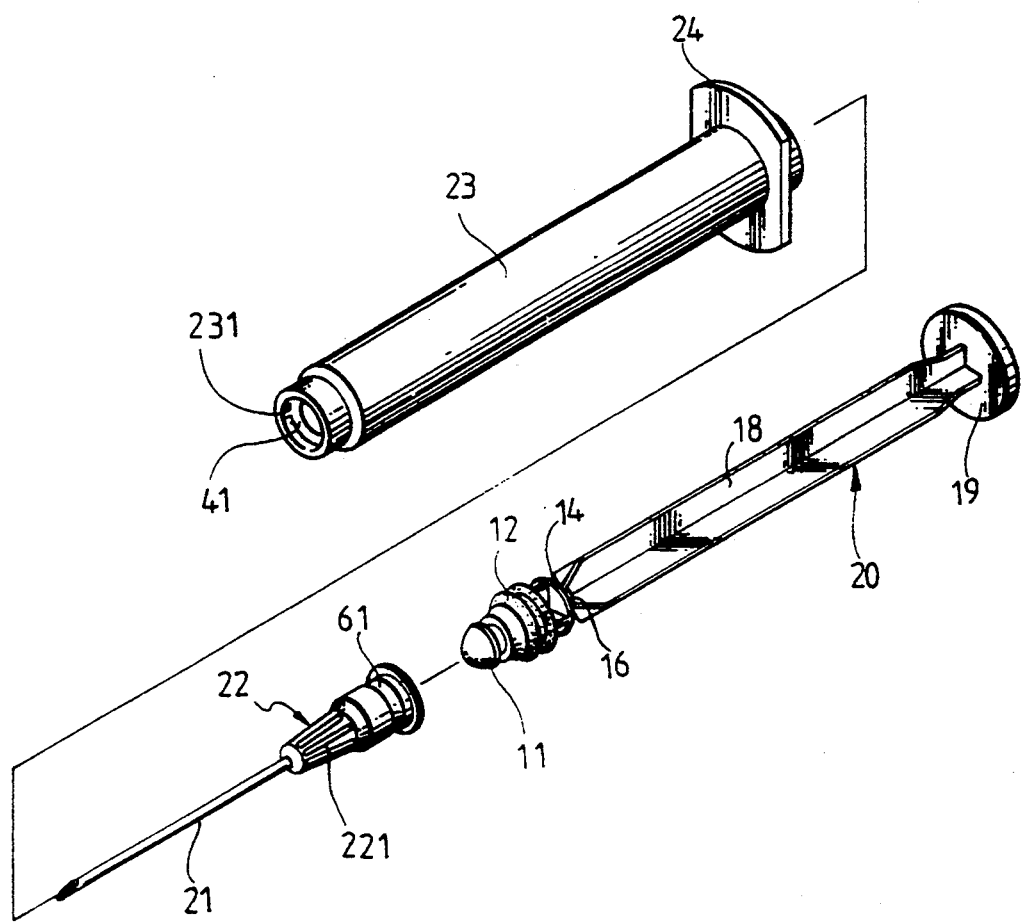
FIG. 1 is an exploded perspective view showing all of the parts of the retractable needle syringe, with concentric barrel opening at the lower end, of the present invention.

FIG. 1 shows the respective parts of this retractable syringe. The syringe in FIG. 1 generally comprises a hollow barrel 23 made of semi-rigid deformable plastic with a finger flange 24 on it. To the left of the barrel is an open end 41 to hold the needle 21 and carrier 22, integral in one piece, within.

This needle and carrier 22 is slidably put into the barrel from the upper open end near finger flange 24 and seated within the distal end 41. The annular groove 61 on the carrier closely matches with the annular bore 231 inside distal end 231, to provide the resistance against the needle and carrier going backwards into the barrel while injecting with this syringe and to prevent leakage of medication or fluid.

A plunger 20 follows the carrier and is slidably placed inside the barrel. This plunger includes a shaft defined by flanges 18, a hub 11, to engage with the carrier for retraction purpose as will be discussed in more detail afterwards, a rubber seal 12 seated around the plunger and, a fragile section with an elliptical disk 14 connected to the four flanges next to it by a conical section 16 extending from the disc half way from the four flanges next to it, which enables the plunger be broken easily at any direction with equal stress concentration or stresses generated on a notch tip between located disk 14 and section 16. Generally plastic materials are notch-sensitive which means that a sharp notch tip results in the plastics behaving as brittle and can be easily broken off, while a plastic with blunt notch makes the material behavior ductile and difficult to break off. Therefore, it is only with the combination design of items 14 and 16 that allows for even stress distribution on the notch tip, no matter what angle or direction a bending force is applied on the plunger to break it off into two pieces.

Figure 2:
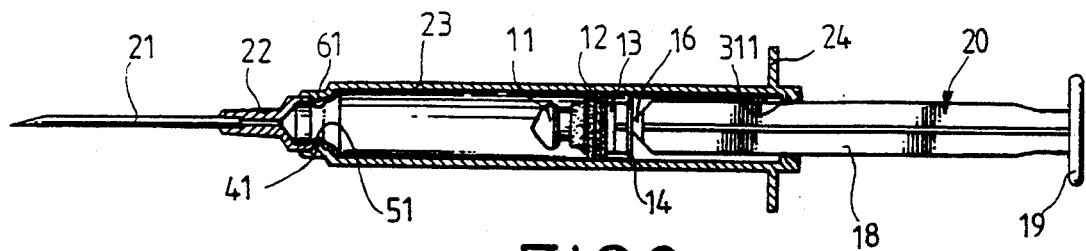
FIG. 2 is a cross-sectional view of the assembled syringe of the present invention.

FIG. 2 gives the cross-sectional view of the assembled syringe of our design of the syringe. A needle 21 sits right in the carrier 22 which in turn fits closely within the distal end 231 to the left of hollow cylindrical barrel 23 by a groove 61 on the carrier 22 and a bore 41 on the inner wall of the distal end 231. The hub 11 on the plunger 20 is elliptical in shape and is larger than the diameter of the bore 51 in order to snug into the carrier 22 through bore 51. The structural shape and dimension of the space inside the carrier 22 and of the hub 11 on the plunger 20 are so designed that as the plunger 20 is pushed to the lower end and the hub 11 is just in contact with the bore 51 but just before going through the bore 51 for retraction, the dead space between the carrier 22 and the hub 11 containing residual medication or fluid is thus minimized to be no greater than that of the conventional syringes. It is in practice at this stage before the hub 11 going through the bore 51 that the physicians or nurses practicing the injection should withdraw the needle from the skin of the patient to avoid pain from that further push of the plunger in the human tissue. In FIG. 2, part 14 is an elliptical disk being able to go through the bore 311 at the right of the upper end of the barrel 23, but serves as a stop for the plunger from leavning the barrel when retracting, as will be discussed in more detail in FIG. 4.

Figure 3:
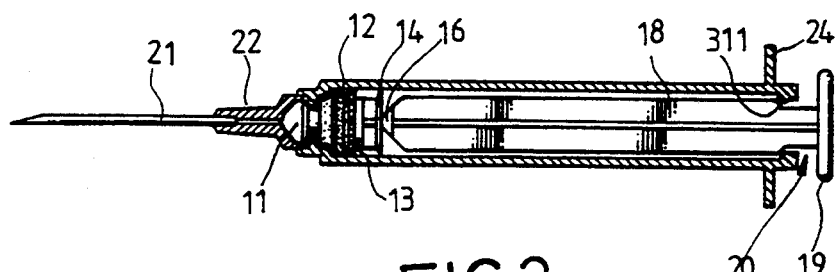
FIG. 3 is a cross-sectional view of the assembled syringe after injection, with the plunger hub locked onto the needle carrier, ready to be retracted into the barrel.

FIG. 3 is the cross sectional view of the retractable syringe after injection and the plunger is pushed further to engage with the carrier. Now the carrier is ready for retraction into the barrel by pulling the plunger. From the instinct, it seems that there is no space left for the residual air possibly existing in the medication or fluid to stop the residual air from going into the artillery or human tissue, if an injector carelessly push the plunger all the way down to the end through the bore 51, although the injector is supposed to stop just before the hub 11 going through the bore 51. However, if an injector follows the procedures and stop injection by feeling from the finger tips that the hub 11 is just right in front of the bore 51, and pull out the needle from the skin, there is no chance for air to go into the artillery or human tissue. Even when an injector carelessly pushed the plunger and the hub 11 all the way down to the bottom through the bore 51, although it is very unlikely to happen, because the hub 11 is elliptical in shape, there is still room for the residual air if there is. This can hardly be seen from the drawing in FIG. 3 since the drawing is to indicate the engagement mechanism of the hub with the carrier. The room allocated for the accommodation of the residual air, if any, can better be understood from a top view not shown, instead of the side cross sectional view.

Figure 4:
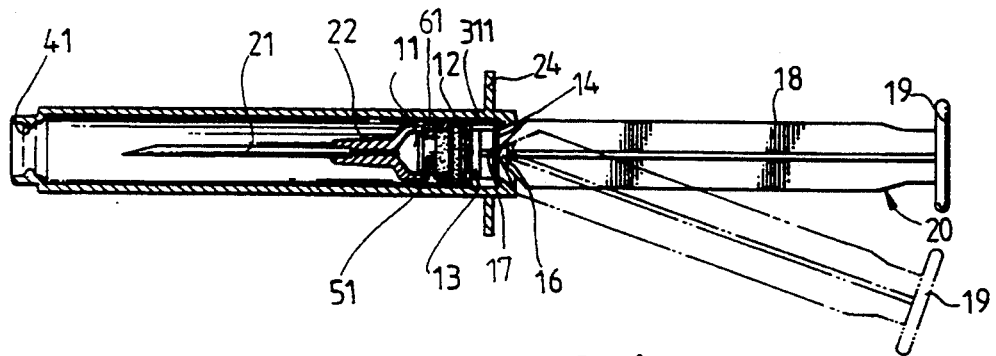
FIG. 4 is a cross-sectional view of the assembled syringe, with the carrier retracted into the barrel and the plunger broken off at the fragile section.
Figure 6:
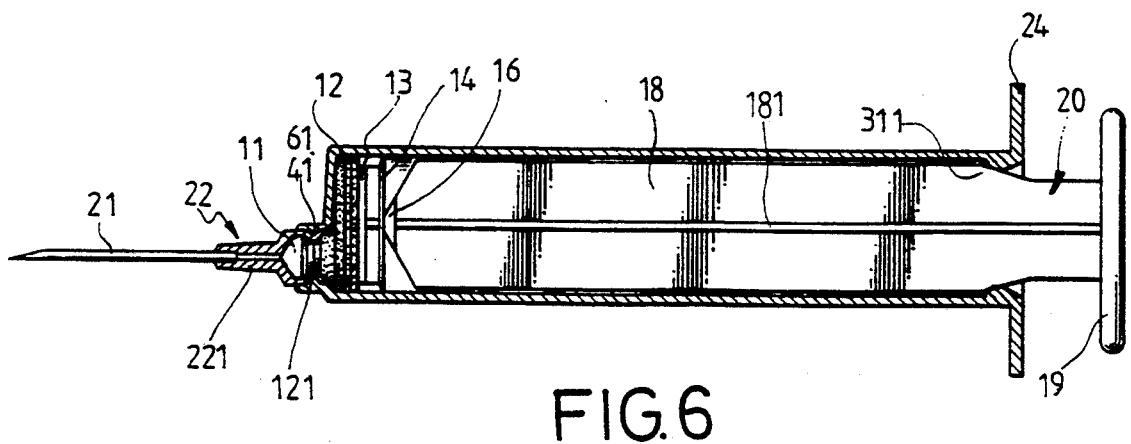
FIG. 6 is a cross-sectional view of the assembled syringe with eccentric barrel opening, after injection; the plunger hub is locked onto the needle carrier, ready to be retracted into the barrel.
Figure 5:
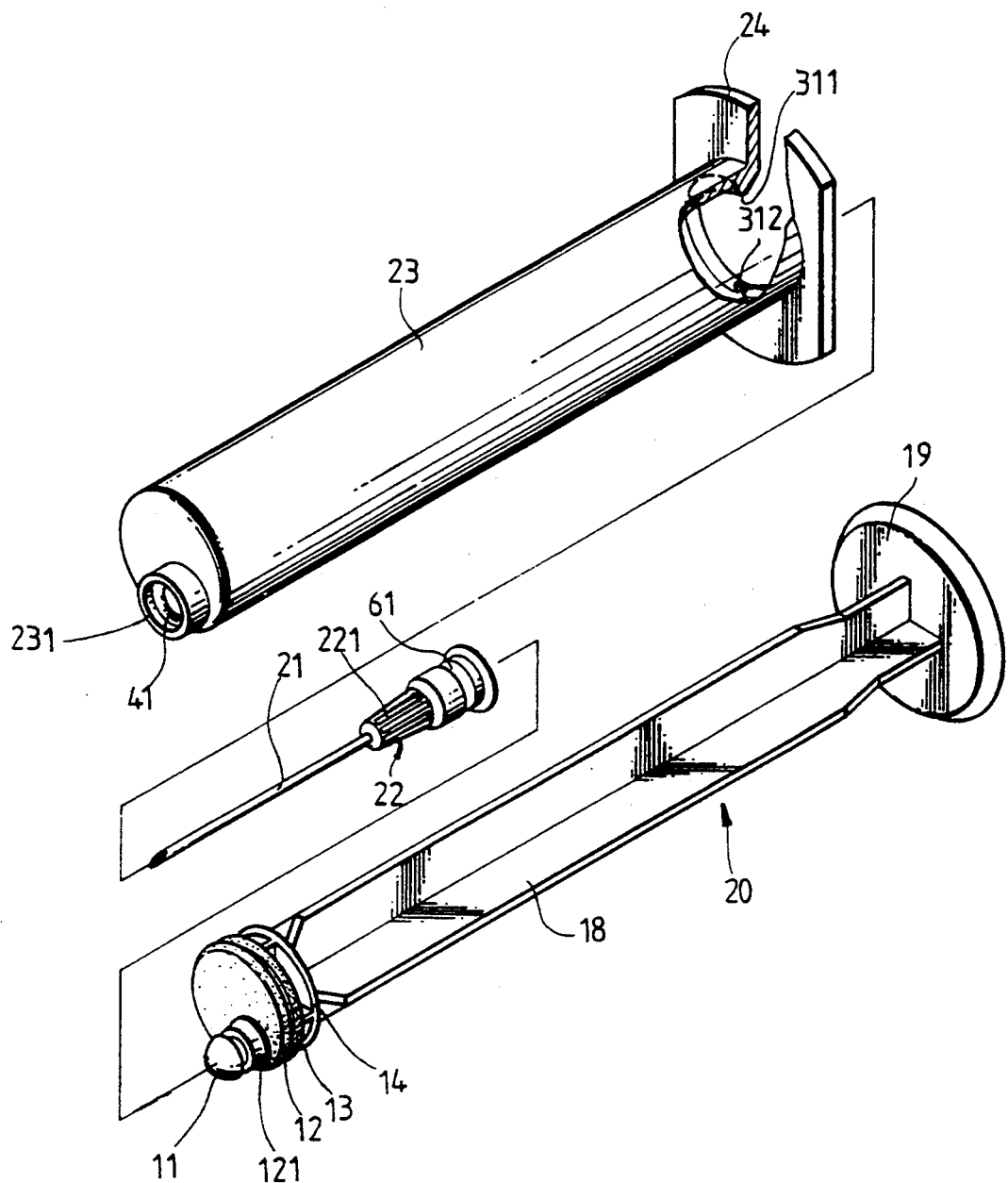
FIG. 5 is an exploded perspective view showing all of the parts of the retractable needle syringe, with eccentric barrel opening to the side of the barrel, of the present invention.

As the plunger retracts the carrier with the needle into the barrel and come to a stop and break, the detailed drawing of the cross sections are shown in FIG. 4. While the plunger pulls backwards the carrier and the elliptical disk 14 is in contact with the bore 311 on the inner wall at the upper end of the barrel, the plunger can be easily broken off at the fragile section between parts 14 which is a solid elliptical piece and 16, no matter what angle around the shaft is the bending force applied onto the plunger. While FIG. 5 gives the respective parts of our retractable syringe design suitable for higher volume capacity, for example a 20 c.c. syringe, in which the needle is located eccentric to the side of the cylindrical barrel, for easier injection into the skin, or artillery. The structure of the hollow cylindrical barrel is basically similar to that of FIG. 1, except that the bore 311 inside the upper open end has 4 open slots 312 having just enough room for the four flanges 18 which form the shaft of on the plunger 20 to go through. The plunger is not allowed to rotate relative to the barrel; it can only move slidably along the axis of the barrel for accurate positioning of the hub 11 into the carrier 22, which both are eccentric to the sides of the barrel and the plunger respectively. The needle 21 and carrier combination 22 basically is the same as the needle and carrier combination in FIG. 1 except that the needle length and diameter will be different. Part 14 is also an elliptical disk for stopping the plunger as it retracts, and 16, not seen in FIG. 5 but seen in FIG. 6, is a solid concial piece. Parts 14 and 16 result in even stress concentration in the sharp notch region between them which is the fragile section of the plunger for easy breaking off after retraction, same as those described in FIG. 1. FIG. 6, illustrates the cross sectional view of the assembled syringe for the parts in FIG. 5, very similar to the indications given to FIG. 3, except that the bore 311 at the upper end of FIG. 5 has 4 slots 312 for flanges 18 to go slidably but not rotatably, while the bore 311 in FIG. 3 does not have slots and therefore the plunger in FIG. 3 can go slidably and rotatably.

What is claimed is:

1. A retractable safety syringe comprising:
   a hollow cylindrical barrel having an open upper end, an open lower end, an inwardly projecting lip at the lower end and a finger flange at the upper end;
   a cylindrical needle carrier mounted within said barrel, seated on said lip and retained in place by engagement between an internal circumferential ridge on said lip and a circumferential groove in an outer peripheral wall of said needle carrier, said needle carrier having an extension protruding through the lower end of said barrel and an enlarged extension facing the upper end of said barrel to aid in retaining said carrier in place during use;
   a hypodermic needle embedded within said extension of said carrier;
   a plunger slidably mounted in said barrel through the upper end and defining a fluid chamber between said carrier and said plunger;
   a central bore through said carrier and extension for fluid communication between said needle and said chamber;
   a shaft having a longitudinal axis extending from an upper end of said plunger through the upper end of the barrel for depressing the plunger;
   a hub extending from a lower end of said plunger adapted to lock into said bore for withdrawing the needle carrier and needle into the barrel;
   a rubber seal around said plunger; and
   a conical section between the plunger and the shaft defining a sharp notch above said plunger to allow said shaft to be broken off in any angular direction about the longitudinal axis when the needle carrier and needle are withdrawn into the barrel.

2. A syringe as claimed in claim 1, wherein the plunger includes a disk at its upper end, the shaft comprises a plurality of radially extending flanges and said conical section extends between said disk and said flanges, said flanges tapering inwardly to merge with the conical section.

3. A syringe as claimed in claim 1, wherein said lip is eccentric to a longitudinal axis of the barrel and the hub is correspondingly eccentric to a longitudinal axis of the plunger.

4. A syringe as claimed in claim 1, wherein the plunger includes an elliptical disk adjacent said conical section and the barrel includes an internal rim at the upper end to retain the disk within the barrel.

5. A syringe as claimed in claim 4, wherein the shaft comprises radially extending flanges and said internal rim has slots receiving the flanges.

6. A syringe as claimed in claim 1, wherein the hub is elliptical.

* * * * *